United States Patent [19]

Kawamatsu et al.

[11] 4,080,505
[45] Mar. 21, 1978

[54] α-CHLOROCARBOXYLIC ACIDS

[75] Inventors: Yutaka Kawamatsu, Kyoto; Takahiro Saraie, Osaka; Eiko Imamiya, Tondabayashi; Yukihiko Hamuro, Hyogo, all of Japan

[73] Assignee: Takeda Chemical Industries, Japan

[21] Appl. No.: 692,577

[22] Filed: Jun. 3, 1976

[30] Foreign Application Priority Data

Jun. 9, 1975 United Kingdom .............. 24666/75
Sep. 29, 1975 Japan ................................ 50-118099
Apr. 19, 1976 Japan ................................ 51-44870

[51] Int. Cl.² .......................................... C07C 69/76
[52] U.S. Cl. ................. 560/55; 260/520 R;
260/521 H; 260/552 R; 260/553 A; 260/612 R;
260/559 B; 560/53; 424/308
[58] Field of Search ................................... 260/473 R

[56] References Cited

U.S. PATENT DOCUMENTS 3,983,164  9/1976  Thorne et al. .................. 260/473 R Primary Examiner—Paul J. Killos
Attorney, Agent, or Firm—Wenderoth, Lind & Ponack

[57] ABSTRACT

α-chlorocarboxylic acids of the formula

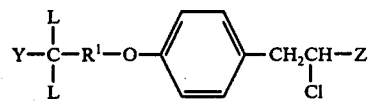

wherein Y stands for a lower alkyl group having 1 to 6 carbon atoms or a phenyl group, a benzoyl group or a phenylalkyl group having 7 to 11 carbon atoms, which may have a lower alkyl group having 1 to 3 carbon atoms, a lower alkoxy group having 1 to 3 carbon atoms or a halogen on the phenyl rings as a substituent; $R^1$ stands for a lower alkylene group having 1 to 4 carbon atoms or a valency bond; L stands for a lower alkyl group having 1 to 3 carbon atoms; and Z stands for a carboxyl group or a group convertible to carboxyl group, are useful as, for example, remedies for hyperlipemia, diabetes and so on of mammals including human beings.

15 Claims, No Drawings

α-CHLOROCARBOXYLIC ACIDS

The present invention relates to novel α-chlorocarboxylic acids of the formula (I):

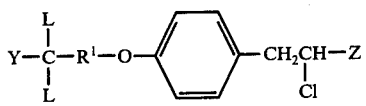

wherein Y stands for a lower alkyl group having 1 to 6 carbon atoms or a phenyl group, a benzoyl group or a phenylalkyl group having 7 to 11 carbon atoms, which may have a lower alkyl group having 1 to 3 carbon atoms, a lower alkoxy group having 1 to 3 carbon atoms or a halogen on the phenyl rings as a substituent; $R^1$ stands for a lower alkylene group having 1 to 4 carbon atoms or a valency bond; L stands for a lower alkyl group having 1 to 3 carbon atoms; and Z stands for a carboxyl group or a group convertible to a carboxyl group, and to process for preparing these α-chlorocarboxylic acids.

The present inventors have made an extensive study of a series of α-chlorocarboxylic acids and succeeded in synthesizing the novel compounds of the above formula (I), and have found out that the above compounds have remarkable hypolipidemic, hypoglycemic and other biological activities.

Thus, the principal object of this invention is to provide novel compounds of the formula (I) useful as, for example, remedies for hyperlipemia, diabetes and so on in mammals including human beings.

Another object of this invention is to provide methods for producing these novel compounds.

Further objects will be made apparent from the description and claims hereinafter given.

The symbol $R^1$ represents a lower alkylene group, e.g. methylene, ethylene, trimethylene, butylene or the like; or a valency bond. The term "valency bond" is one referred to by such symbols as [—], [.], and so on, which are commonly used in chemical structural formulae. When $R^1$ represents valency bond, the carbon atom at one side of $R^1$ directly combines with the oxygen atom at the other side of $R^1$ and the compound of formula [I] is shown as below.

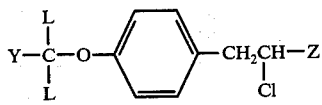

The symbol L represents a lower alkyl group having 1 to 3 carbon atoms, e.g. methyl, ethyl or the like. The symbol Y represents a lower alkyl having 1 to 6 carbon atoms (e.g. methyl, ethyl, n-propyl, isopropyl, n-butyl, t-butyl, n-pentyl, n-hexyl etc.), a phenyl, a benzoyl or phenylalkyl having 7 to 11 carbon atoms (e.g. benzyl, phenethyl, phenylpropyl, phenylbutyl, etc.). Each of the phenyl, benzoyl and phenylalkyl may have a substituent on the phenyl rings, and the substituent includes a lower alkyl having 1 to 3 carbon atoms (e.g. methyl, ethyl, etc.), a lower alkoxy having 1 to 3 carbon atoms (e.g. methoxy, ethoxy, etc.) and a halogen atom (i.e. fluorine, chlorine, bromine, iodine).

The symbol Z designates carboxyl group or a group convertible to carboxyl group. As the group convertible to carboxyl group, there may be mentioned, for example, a group represented by the formulae: —$COOR^2$ (wherein $R^2$ represents a lower alkyl having 1 to 4 carbon atoms, e.g. methyl, ethyl, n-propyl, i-propyl, n-butyl, t-butyl, etc.), $CONH_2$, $CONHR^3$ (wherein $R^3$ represents a lower alkyl having 1 to 3 carbon atoms, e.g. methyl, ethyl, n-propyl, etc., cycloalkyl having 3 to 6 carbon atoms, e.g. cyclopropyl, cyclopentyl, cyclohexyl, etc. or aryl having 6 to 10 carbon atoms, e.g. phenyl, chlorophenyl, tolyl, methoxyphenyl, etc.), $CONR^4R^5$ (wherein each of $R^4$ and $R^5$ have the same meanings as that of $R^3$) or

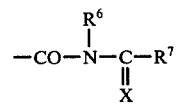

(wherein $R^6$ represents hydrogen or a lower alkyl having 1 to 3 carbon atoms, e.g. methyl, ethyl, etc., X represents oxygen or sulfur and $R^7$ represents a lower alkyl having 1 to 3 carbon atoms, e.g. methyl, ethyl, etc., amino, mono or dialkylamino having 1 to 6 carbon atoms, e.g. N-methylamino, N,N-dimethylamino, N-ethylamino, N,N-diethylamino, N-propylamino, etc. or mono or diarylamino having 6 to 20 carbon atoms, e.g. N-phenylamino, N,N-diphenylamino, N-naphthylamino, etc.).

The mono- or di-substituted aminocarbonyl groups represented by $CONHR^4$ or $CONR^5R^6$ may include, among others, mono- or di-alkylaminocarbonyl groups such as N-methylaminocarbonyl, N,N-dimethylaminocarbonyl, N-ethylaminocarbonyl, N,N-diethylaminocarbonyl, N-propylaminocarbonyl, N,N-dipropylaminocarbonyl, N-isopropylaminocarbonyl, N,N-diisopropylaminocarbonyl or N-butylaminocarbonyl; mono- or dicycloalkylaminocarbonyl groups such as N-cyclopentylaminocarbonyl, N,N-dicyclopentylaminocarbonyl, N-cyclohexylaminocarbonyl or N,N-dicyclohexylaminocarbonyl; and mono- or diarylaminocarbonyl groups such as N-phenylaminocarbonyl, N,N-diphenylaminocarbonyl, N-tolylaminocarbonyl or N,N-ditolylaminocarbonyl.

When Z represents carboxyl group, the compound (I) may be in a form of such salt at the carboxyl group as alkali metal salt (e.g. COONa, COOK, COOLi, etc.) alkaline earth metal salt (e.g. $COOCa_½$, $COOMg_½$, etc.), ammonium salt, ammonium salt (e.g. $COCAl_½(OH)_½$, $COOAl_⅓$, etc.), an organic amine salt (polyhydroxyalkylamine salt, e.g. N-methylglucamine salt, diethanolamine salt, triethanolamine salt, tris-hydroxymethylaminomethane salt, etc.) and so on.

The compound of formula (I) can be prepared by the various process steps described below.

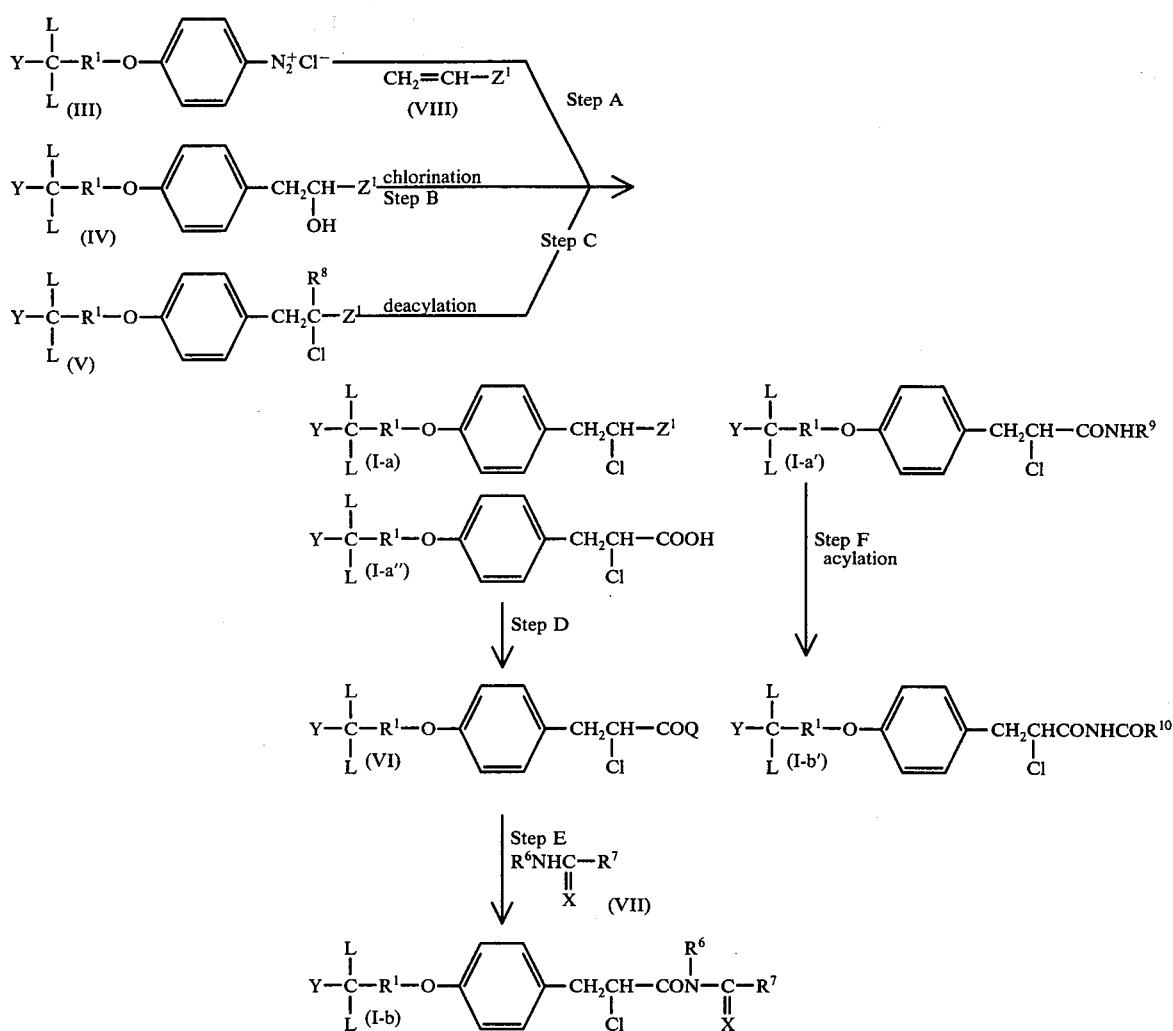

In the above, $R^8$ represents a lower acyl group having 2 to 5 carbon atoms e.g. acetyl, pripionyl, butyryl, isobutyryl, valeryl, isovaleryl, etc. $R^9$ represents hydrogen or carbamoyl. $R^{10}$ represents a lower alkyl having 1 to 3 carbon atoms, e.g. methyl, ethyl, etc. Q represents a halogen e.g. chlorine, bromine, etc. $Z^1$ represents the same meaning as Z except a group;

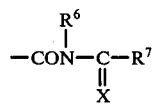

The reaction of Step A is carried out by reacting a diazonium salt (III) with vinyl compound (VIII). It is usually desirable to react the diazonium salt (III) with a stoichiometrically slight excess of vinyl compound (VIII). Unless the reaction is thereby adversely affected, the vinyl compound (VIII) may be employed in a large excess. The reaction is usually conducted in a solvent. Among the more common species of solvent are water, acetone, methyl ethyl ketone, diethyl ketone, ethyl propyl ketone, acetonitrile, N-methylpyrrolidone, dimethylsulfoxide and sulfolane, as well as various mixtures thereof. This reaction may be conducted to greater satisfaction by adding a hydrogen chloride such as hydrochloric acid or the like. For example, when a solvent containing hydrogen chloride is used, a diazonium salt (III) having an anion other than a chlorine atom can be used as a starting material in this reaction. This is apparently due to the fact that the anion other than a chlorine atom is replaced by the hydrogen chloride in the solvent to yield the diazonium salt (III). This reaction proceeds more satisfactorily in the presence of a catalyst. As the catalyst for this purpose, use may be made of, for example, a copper compound, the common useful species of which include cuprous oxide, cupric oxide, cuprous chloride, cupric chloride, cuprous bromide, cupric bromide, copper nitrate, copper sulphate, cuprous cyanide or copper acetate. Cuprous oxide, in particular, gives satisfactory results. Usually the proportion of the catalyst is from 0.02 to 0.4 mole, preferably 0.05 to 0.2 mole, per mole of diazonium salt (III).

To control the reaction velocity, the aforementioned catalyst may be used in a large amount or in a very small amount. The conditions such as temperature, time and pressure are chosen according to such factors as the starting materials, the solvent and the catalyst. Usually, the reaction proceeds at temperatures of from below room temperature (under cooling) to 50° C. The reaction time is usually 1 to 5 hours.

The α-chlorocarboxylic acids (I-a) thus obtained can be isolated and purified by known separate procedures such as e.g. concentration, concentration under reduced pressure, distillation, distillation under reduced pressure, fractional distillation, pH adjustment, solvent extraction, crystallization, recrystallization, phasic transfer and chromatography.

The reaction of Step B is carried out by allowing a chlorinating agent to act upon an α-oxypropionic acids (IV). As the chlorinating agent, there may be employed chlorinating agents which can convert the hydroxyl group at the α-position of the starting compound (IV) to a chlorine atom. The chlorinating agent may be exemplified by, for example, thionyl chloride, phosphorous oxychloride, phosphorous trichloride, titanium tetrachloride, hydrogen chloride, phosphorous pentachloride or the like. The chlorinating agent is normally usually in an amount of about one mole equivalent to the α-oxypropionic acid (IV). but may be reacted in an excess of the mole equivalent relative to the starting compound (IV), provided it does not adversely affect the reaction. If necessary, a suitable solvent may be used in this reaction. The suitable solvent may be, for example, chloroform, carbon tetrachloride, an ether (e.g. diethylether, tetrahydrofuran or dioxane), an aromatic hydrocarbon (e.g. benzene, toluene or xylene) or the like. A catalytic amount of a base may be added to cause the reaction to proceed more smoothly. As the bases, there may be used, for example, pyridine, quinoline, triethylamine and the like. The reaction is usually conducted at a temperature ranging 20° to 110° C for 0.5 to 20 hours. The α-chlorocarboxylic acids (I-a) thus obtained can be isolated and purified by known procedures as mentioned above.

The reaction of Step C is carried out by subjecting a compound (V) to a deacylating reaction. In the deacylating reaction, a suitable method which can convert the lower acyl group on the α-position of the compound (V) to a hydrogen atom is employed. For example, the conversion can be attained by allowing a base to act upon the compound (V).

As the bases, use may be made of, for example, barium hydroxide, sodium hydroxide, potassium hydroxide, sodium carbonate, potassium carbonate or the like. The base may be used in an amount of about one mole equivalent or a slight excess relative to the compound (V). The reaction is, usually, desirably conducted under substantially anhydrous conditions. The solvents used in this reaction may be exemplified by, e.g., alcohols such as methyl alcohol, ethyl alcohol, propyl alcohol, isopropyl alcohol or butyl alcohol, ethers such as diethylether, tetrahydrofuran or dioxane; or mixtures thereof, and these solvents are desirably used under substantially anhydrous conditions. This reaction is usually conducted at a temperature ranging −10° to 10° C for 1 to 120 minutes.

The resulting α-chlorocarboxylic acids (I-a) may be isolated and purified by the known methods described hereinbefore.

The α-chlorocarboxylic acids (I-a) obtained by the foregoing method of this invention, when $Z^1$ represents a carboxyl group, can be used as they are, i.e. with the carboxyl group in the free acid or after conversion in a conventional manner to a salt with a cation, e.g. sodium, potassium, calcium, lithium, magnesium, ammonium or an organic amine such as a polyhydroxyalkylamine, e.g. N-methylglucamine, diethanolamine, triethanolamine, trishydroxymethylaminomethane, or the like; to an ester such as the methyl ester, ethyl ester, propyl ester, isopropyl ester or the like; or to the corresponding amides.

When $Z^1$ in the α-chlorocarboxylic acid compounds (I-a) represents a group convertible to carboxyl group, the first-mentioned group may be converted to a carboxyl group in a conventional manner. For example, when $Z^1$ is an alkoxycarbonyl group or an unsubstituted or substituted aminocarbonyl group, it can be converted to a carboxyl group by subjecting the compounds (I-a) to conventional hydrolysis. To mention a specific example, the hydrolysis can be effected by treating the α-chlorocarboxylic acid compounds (I-a) with an acid, such as hydrochloric acid, sulphuric acid or the like, or a base such as sodium hydroxide, potassium hydroxide, sodium carbonate, potassium carbonate or the like. If necessary, the hydrolysis may be conducted in the presence of an alcohol such as methyl alcohol, ethyl alcohol or the like. The hydrolysis is usually conducted at a temperature ranging 20° C to 130° C for 0.5 to 30 hours.

Among the compounds (I-a) obtained in the above mentioned process A, B or C, the compound (I-a'') can be introduced into the compound (I-b) through the Steps D and E, and further the compound (I-a') can be introduced into the compound (I-b') through Step F.

The reaction of Step D is carried out by reacting a compound (I-a'') with a halogenating agent. As the halogenating agent, there may be mentioned by thionyl chloride, thionyl bromide, phosphorus oxychloride, phosphorus trichloride, phosphorus pentachloride, titanium chloride, etc. This reaction is conducted in the presence or absence of a solvent. As the solvent, aromatic hydrocarbon such as benzene, toluene, etc. is advantageously used. The halogenating agent is usually used in an amount of 1.0 to 1.2 mole per one mole of compound (I-a''). However, when a large excess amount of halogenating agent is used, the use of a solvent is unnecessary. The reaction is usually carried out at room temperature to boiling point of the reaction system for about 1 to 5 hours. The compound (VI) thus obtained may be subjected to the following reaction of Step E without subjecting isolation.

The reaction of Step E is carried out by reacting an acid halide (VI) with an amide (VII). This reaction is usually conducted in a solvent. As the solvent, aromatic hydrocarbon such as benzene, toluene, etc. and ether such as tetrahydrofuran, dioxane, etc. are advantageously used. Though the contacting ratio of acid halide (VI) and amide (VII) is not limited, the amide (VII) is usually used in a little excess amount relative to the acid halide (VI). In order to let proceed the reaction smoothly, an acid (sulfuric acid, etc.) or a base (pyridine, etc.) is advantageously added to the reaction system. The amount of these substances to be added is usually 0.01 to 2 moles, preferably 0.1 to 0.5 mole, per mole of acid halide (VI). Though other conditions such as the reaction temperature and time are suitably chosen depending on such factors as the starting compounds (VI), solvent and so on, the reaction is usually conducted at room temperature to the boiling point of the reaction system for 1 to 5 hours.

The resulting α-chlorocarboxylic acids (I-b) can be isolated and purified by the known methods described hereinbefore.

The reaction of Step F is carried out by reacting an amide (I-a') with an acylating agent. As the acylating agent, acyl halide such as acetyl chloride, acetyl bromide, propionyl chloride, etc. and acid anhydride such as acetic anhydride, propionic anhydride, benzoic anhydride, etc. are employed.

The acylating agent is usually employed in an amount of 1 to 3 moles per mole of amide (I-a'). An excess amount of acylating agent may be employed unless adversely affected. This reaction is conducted in the presence or absence of a solvent. As the solvent, an aromatic hydrocarbon such as benzene, toluene, etc. and organic carboxylic acid such as acetic acid, etc. are mentioned. In order to proceed the reaction smoothly, a small amount of sulfuric acid, zinc chloride, aluminum chloride, etc. may be added to the reaction system. Though the conditions such as the reaction temperature and time are suitably chosen depending on such factors as the starting compounds (I-a'), solvent and so on, the reaction is usually conducted at 80° to 130° C, preferably at 100° to 110° C, for about 1 to 3 hours.

The resulting α-chlorocarboxylic acids (I-b') can be isolated and purified by the known methods described hereinbefore.

The diazonium salts (III) for the reaction of Step A may be produced, for example, by diazotizing the corresponding amino compound in the presence of hydrogen chloride in a conventional manner or by allowing hydrogen chloride to act upon a diazonium salts (III) having an anion other than a chlorine atom.

Other starting materials (IV) and (V) can be prepared, for example, by the reaction illustrated in the following scheme:

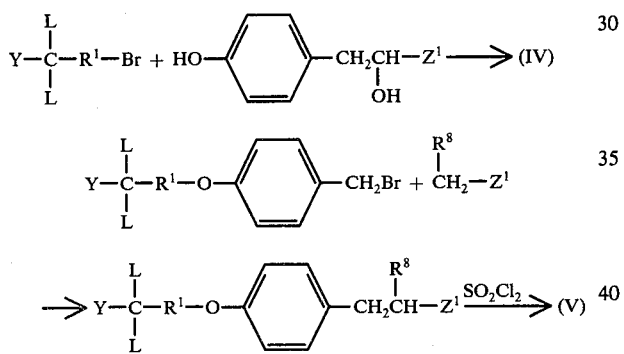

in which each of the symbols is as defined above.

The α-chlorocarboxylic acids (I) thus obtained have prominent hypolipidemic and hypoglycemic activities with an extremely low toxicity and are, therefore, of value as, for example, remedies for hyperlipemia and diabetes of mammals including human beings.

Thus, the desired compounds (I) of this invention are several times as potent as commercial remedies for hyperlipemia such as ethyl 2,2-dimethyl-2-(4-chlorophenoxy)-acetate and are also different from the latter drugs in their mode of action.

The compounds (I) may be administered orally in such dosage forms as tablets, capsules, powders or granules, or by other routes, in such forms as injections, suppositories or pellets, for example. The dosage is such that, compound (I), is used as a remedy for hyperlipemia, the ordinary daily adult dose of 0.05 g to 0.3 g is administered orally or by other routes. As antidiabetics, these compounds are each used as a daily dose level of from 0.05 to 1 g per adult human, orally or by other routes.

The invention is illustrated by the following reference examples and examples.

Throughout the present specification, the abbreviations "g.", "ml", "m.p." and "° C", respectively refer to "gram(s)", "milliliter(s)", "melting point" and "degree(s) centigrade".

REFERENCE EXAMPLE 1

(a) In 200 ml of dimethylsulfoxide are dissolved 23 g of 4-nitrochlorobenzene and 25 g of 2,2-dimethyl-2-phenylethylalcohol. To this solution is added 4 g of sodium hydride is added with stirring. After 24 hours stirring at room temperature and another 30 minutes stirring at 60° C, 500 ml of water is added and the mixture is extracted with ether. The extract is washed with water, dried and the solvent is evaporated. Recrystallization of the residue from 200 ml of methanol, gives 28.5 g of 4-(2,2-dimethyl-2-phenylethyloxy)nitrobenzene, melting point: 79°–80° C.

IR spectrum (cm$^{-1}$, nujol); 1501, 1340

NMR spectrum (δ ppm, CDCl$_3$); 1.47 (6H,s), 4.03(2H,s), 6.87 (2H,d), 7.35(5H,m), 8.13(2H,d).

(b) In a mixed solvent of benzene (60 ml) and methanol (40 ml), 20 g of the nitro compound obtained above (a) and 1.5 g of 10% palladium on charcoal are added and the mixture is shaken in hydrogen atmosphere. After the absorption of hydrogen (5.25 l) ceased, the catalyst is filtered away and the solvent is evaporated.

The oily product of 4-(2,2-dimethyl-2-phenylethyloxy)-aniline is obtained. Yield: 17.1 g IR spectrum (cm$^{-1}$, liquid film); 3450, 3370, 1620

NMR spectrum (δ ppm, CDCl$_3$); 1.20(6H,s), 3.19(2H,s,NH$_2$), 4.83(2H,s), 6.57(4H,q), ca. 7.3(5H,m).

REFERENCE EXAMPLE 2

(a) By a similar manner to reference example 1, 1,1-dimethyl-2-phenylethylalcohol and 4-nitrofluorobenzene are used in place of 2,2-dimethyl-2-phenylethylalcohol and 4-nitrochlorobenzene respectively to give 4-(1,1-dimethyl-2-phenylethyloxy)-nitrobenzene. Melting point: 78°–79° C.

IR spectrum (cm$^{-1}$, liquid film); 1605, 1590, 1515, 1490, 1350

NMR spectrum (δ ppm, CDCl$_3$); 1.30(6H,s), 3.00(2H,s), 6.96 (2H,d), 7.16(5H,s), 8.06(2H,d)

(b) The nitro compound obtained above a) is reduced in the presence of palladium on charcoal with hydrogen by a similar manner to reference example 1-b).

Oily product of 4-(1,1-dimethyl-2-phenylethyloxy)-aniline is obtained.

IR spectrum (cm$^{-1}$, liquid film); 3450, 3375, 1620, 1520

NMR spectrum (δ ppm, CCl$_4$); 1.10(6H,s), 2.85(2H,s), 3.33 (2H,NH$_2$), 6.36(2H,d), 6.60(2H,d), 7.06(5H,s)

REFERENCE EXAMPLE 3

(a) In 15 ml of dimethylformamide, 11.4 g of 2-bromo-2-methylpropiophenon and 7.6 g of 4-acetaminophenol are dissolved and with stirring at room temperature 7.7 g of potassium carbonate is added. After four hours stirring, the solvent is evaporated under reduced pressure and to the residue is added 300 ml of water and 150 ml of benzene.

The crystalline mass precipitated is filtered and dried to give 10.5 g of 2-methyl-2-(4-acetamidophenoxy)-propiophenon. Melting point: 141°–142° C.

IR spectrum (cm$^{-1}$ nujol); 3250, 1680, 1660, 1506, 1140

NMR spectrum (δ ppm, CDCl$_3$): 1.67(6H,s), 2.00(3H,s), 6.57–7.47(7H,m), 7.90(1H,br), 8.17–8.33(2H,m)

(b) In 40 ml of 6N hydrochloric acid 5.6 g of the acetamido compound obtained above (a) is refluxed for one hour. The oily product is extracted with benzene, the extract is washed with dil-NaOH, then with water, dried and the evaporation of the solvent gives oily product of 4 g of 2-methyl-2-(4-aminophenoxy)propiophenon.

IR spectrum (cm$^{-1}$, liquid film); 3450, 3370, 3220, 1675, 1505, 1230, 1165

NMR spectrum ($\delta$ ppm, CDCl$_3$); 1.60(6H,s), 3.37(2H,br), 6.33–6.70(4H,m), 7.17–7.47(3H,m), 8.17–8.40(2H,m).

REFERENCE EXAMPLE 4

In 20 ml of ethanol is dissolved 1.4 g of ethyl 2-hydroxy-3-(4-hydroxyphenyl)propionate and to this solution are added 1.5 g of 30% sodium ethylate in ethanol and 1.6 g of 2-bromo-2-methylpropiophenon. The mixture is refluxed for 3 hours and then the solvent is evaporated. The residue is extracted with ether, the extract is washed with water and dried, and the evaporation of ether gives the oily product which is purified with column chromatography 'SiO$_2$ gel). Thus obtained pure ethyl 2-hydroxy-3-[4-(2-benzoyl-2-propyloxy)-phenyl]-propionate.

REFERENCE EXAMPLE 5

With stirring in an ice bath 0.5 g of sulfuryl chloride is added slowly into 1.3 g of ethyl 2-acetyl-3-[4-(2-benzoyl-2-propyloxy)phenyl]propionate. After the bubbling of gas generated is ceased the mixture stands for 30 min. and then, is poured into water and extracted with ether. The extract is washed with water thoroughly, dried, and the solvent is evaporated.

Thus obtained ethyl 2-acetyl-2-chloro-3-[4-(2-benzoyl-2-propyloxy)phenyl]propionate.

REFERENCE EXAMPLE 6

(a) By a similar manner to reference example 1, neopentylalcohol and sodium hydroxide are used in place of 2,2-dimethyl-2-phenylethylalcohol and sodium hydride respectively to give 4-(2,2-dimethylpropyloxy)nitrobenzene. Melting point: 36° C.

IR spectrum (cm$^{-1}$, nujol); 1605, 1595, 1510, 1340

NMR spectrum ($\delta$ ppm, CDCl$_3$); 0.97(9H,s), 3.63(2H,s), 6.86 (2H,d), 8.09(2H,d)

(b) The nitro compound obtained above (a) is reduced in the presence of palladium on charcoal with hydrogen by a similar manner to reference example 1-b).

Oily product of 4-(2,2-dimethylpropyloxy)aniline is obtained.

NMR spectrum ($\delta$ ppm, CDCl$_3$); 0.97(9H,s), 3.30(2H,s,NH$_2$), 3.50(2H,s), 6.53(2H,d), 6.74(2H,d)

REFERENCE EXAMPLE 7

By a similar manner to reference example 4, 3,3-dimethylbutylbromide is used in place of 2-bromo-2-methylpropiophenon to give ethyl 2-hydroxy-3-[4-(3,3-dimethylbutyloxy)phenyl]propionate.

EXAMPLE 1-(a)

In 150 ml of acetone is dissolved 16.8 g of 4-(2,2-dimethyl-2-phenylethyloxy)aniline and, under cooling with ice and stirring, 20 ml of hydrochloric acid, a solution of 6 g sodium nitrite in 20 ml water, 75 ml of ethyl acrylate and 0.3 g of finely divided cuprous oxide are added in the order mentioned. The mixture is stirred at 10° C for 30 minutes and at room temperature for 2 hours. After the reaction has been completed, the reaction mixture is concentrated under reduced pressure and extracted with ether. The ether is distilled off and residual oil is purified by chromatography on silica gel. The described procedure yields 17.7 g of ethyl 2-chloro-3-[4-(2,2-dimethyl-2-phenylethyloxy)phenyl]propionate as a yellowish oily product. Cyclohexane/benzene is used as the eluant solvent (1:1). Boiling point: 205°–206° C/0.9 mmHg Anal. Calcd. for C$_{21}$H$_{25}$ClO$_3$: C, 69.89; H, 6.89; Found: C, 70.53; H, 6.76.

IR spectrum (cm$^{-1}$, liquid film); 1740, 1250

NMR spectrum ($\delta$ ppm, CDCl$_3$); 1.10(3H,t), 1.27(6H,s), 3.13 (2H,m), 3.87(2H,s), 4.07(2H,q), 4.31(1H,t), 6.89 (4H,q), 7.3(5H,m)

EXAMPLE 1-(b)

In 15 ml of ethanol is dissolved 3.6 g of ethyl 2-chloro-3-[4-(2,2-dimethyl-2-phenylethyloxy)phenyl]-propionate, and under cooling with ice and stirring, a solution of 0.35 sodium hydroxide in 3.5 ml water is added. The mixture is kept under the same condition for 30 minutes, after which the solution is concentrated to dryness. The residue is dissolved in 10 ml of water, the solution is washed three times with ether, and then the solution is concentrated to dryness. The procedure yields 2.6 g of sodium 2-chloro-3-[4-(2,2-dimethyl-2-phenylethyloxy)-phenyl]propionate, as white amorphous substance.

Melting point: 169°–170° C (from methanol)

Anal. Calcd. for C$_{19}$H$_{20}$O$_3$ClNa: C, 64.32; H, 5.69; Found: C, 64.57; H, 5.42.

IR spectrum (cm$^{-1}$, KBr); 1600, 1400, 1250, 1040

NMR spectrum ($\delta$ ppm, d$_6$-DMSO); 1.31(6H,s), 2.7–3.4(2H,m), 3.97(2H,s), 4.21(1H,q,), 6.7–7.5(9H,m).

EXAMPLE 1-(c)

In 5 ml of water is dissolved 350 mg of sodium 2-chloro-3-[4-(2,2-dimethyl-2-phenylethyloxy)phenyl]-propionate, followed by the addition of 2-N hydrochloric acid. The oily substance separated out is extracted with ether. The extract is washed with water and the solvent is distilled off. The described procedure gives 300 mg of 2-chloro-3-[4-(2,2-dimethyl-2-phenylethyloxy)phenyl]propionic acid, as a yellow oily substance.

Anal. Calcd. for C$_{19}$H$_{21}$O$_3$Cl: C, 68.57; H, 6.36; Found: C, 68.72; H, 6.19.

IR spectrum (cm$^{-1}$, liquid film); 1710, 1510, 1250, 1040

NMR spectrum ($\delta$ ppm, CDCl$_3$); 1.30(6H,s), 2.8–3.4(2H,m), 3.87(2H,s), 4.39(1H,t), 6.7–7.5(9H,m), 10.20(1H, broad)

EXAMPLE 2

Ethyl-2-chloro-3-[4-(2,2-dimethyl-2-phenylethyloxy)-phenyl]propionate is obtained by a similar manner to example 1-a), using methyl ketone and cupric chloride in place of acetone and cuprous oxide respectively.

EXAMPLE 3

2-chloro-3-[4-(2,2-dimethyl-2-phenylethyloxy)-phenyl)-propionamide is obtained by a similar manner to Example 1-a), using acrylamide in place of ethyl acrylate, as oily substance.

Anal. Calcd. for C$_{19}$H$_{22}$ClNO$_2$: C, 68.77; H, 6.68; N, 4.22 Found: C, 69.10; H, 6.63; N, 4.09

IR spectrum (cm$^{-1}$, liquid film); 3500–3300, 1680, 1515, 1250
NMR spectrum (δ ppm, CDCl$_3$); 1.40(6H,s), 2.8–3.5(2H,m), 3.90(2H,s), 4.40(1H,q), 6.37(2H,br), 6.7–7.5(9H,m)

EXAMPLE 4

In 30 ml of acetone is dissolved 2.6 g of 4-(2-benzoyl-2-propyloxy)aniline and, under cooling with ice and stirring, 3.5 ml of hydrochloric acid, a solution of 0.8 g sodium nitrite in 3 ml water, 7 ml of acrylic acid and 0.7 g of finely divided cuprous chloride are added in the order mentioned. The mixture is stirred at 35° C for 1 hour and at room temperature for 1 hour, after which it is extracted with benzene. The extract is washed three times with water, and then the solvent is distilled off. The residue is dissolved in 10% of aqueous sodium bicarbonate, the solution is washed with benzene and then acidified with hydrochloric acid. The resultant oily substance is extracted with ether and the ether is distilled off to give 2 g of 2-chloro-3-[4-(2-benzoyl-2-propyloxy)phenyl]-propionic acid as a yellow oily substance.

Anal. Calcd. for $C_{19}H_{19}ClO_4$: C, 65.80; H, 5.52; Found: C, 65.52; H, 5.60.

IR spectrum (cm$^{-1}$, liquid film); 1720, 1675, 1510, 1240, 1170, 1150
NMR spectrum (δ ppm, CDCl$_3$); 1.63(6H,s), 2.80–3.43(2H,m), 4.33(1H,q), 6.67(2H,d), 7.00(2H,d), 7.20–8.30(5H,m), 11.37(1H,s)

EXAMPLE 5

In 10 ml of ether, 350 mg of ethyl 2-hydroxy-3-[4-(2-benzoyl-2-propyloxy)phenyl]propionate, 360 mg of thionyl chloride, and catalytic amount of pyridine are added and stirred at room temperature overnight. Then, saturated aqueous sodium bicarbonate solution is added and the ether layer separated is dried, evaporated, and purified with column chromatography. Ethyl-2-chloro-3-[4-(2-benzoyl-2-propyloxy)phenyl]propionate is obtained with the yield of 300 mg. In IR and NMR, this product is in good agreement with the compound No. 1 in Example 7.

EXAMPLE 6

In 3 ml of absolute ethanol, 400 mg of ethyl 2-acetyl-2-chloro-3-[4-(2-benzoyl-2-propyloxy)phenyl]propionate is dissolved and with stirring under ice-cooling, 85 mg of barium hydroxide (dehydrated at 125° C for 8 hours under reduced pressure) is added. After 10 minutes stirring, ether is added and the insoluble material is filtered away. The ether layer is washed with water thoroughly, dried, and the evaporation of the solvent gives the oily product of ethyl 2-chloro-3-[4-(2-benzoyl-2-propyloxy)-phenyl]propionate. In IR and NMR, this product is in good agreement with the compound No. 1 in Example 7.

EXAMPLE 7

By a similar manner to Examples 1 to 6, the following compounds No. 1—22 are produced.

$$Y-\underset{L}{\overset{L}{\underset{|}{\overset{|}{C}}}}-R^1-O-\langle\phantom{O}\rangle-CH_2\underset{Cl}{\overset{|}{C}H}-Z$$

| No. | Product | IR spectrum (cm$^{-1}$, liquid film) | NMR spectrum (δppm, CDCl$_3$) | M.P. (° C) | Used Example |
|---|---|---|---|---|---|
| 1 | Y=⟨phenyl⟩—CO—<br>L=CH$_3$—<br>R$^1$=—<br>Z=COOC$_2$H$_5$ | 1745<br>1680<br>1510<br>1240<br>1170 | 1.17(3H,t), 1.70(6H,s), 2.77–3.50(2H,m), 4.13(2H, q), 4.53(1H,t), 6.63(2H, d), 6.90(2H,d), 7.20–7.40 (3H,m), 8.10–8.30(2H,m) | Oil | 1-(a), 2 |
| 2 | Y=⟨phenyl⟩—CH$_2$—<br>L=CH$_3$—<br>R$^1$=—<br>Z=—COOC$_2$H$_5$ | 1740<br>1605<br>1505<br>1230<br>1170 | 1.19(3H,t), 1.24(6H,s), 2.89–3.54(2H,m), 2.96(2H,s), 4.17(2H,q), 4.40(1H,t), 6.91(2H,d), 7.10(2H,d), 7.27(5H,s) | Oil | 1-(a) |
| 3 | Y=⟨phenyl⟩—CH$_2$CH$_2$—<br>L=CH$_3$—<br>R$^1$=—<br>Z=—COOC$_2$H$_5$ | 1740<br>1240<br>1165<br>700 | 1.17(3H,t), 1.30(6H,s), 1.77–2.07(2H,m), 2.67–3.50(4H,m), 4.10(2H,q), 4.37(1H,t), 6.77–7.13(9H,m) | Oil | 1-(a) |
| 4 | Y=⟨phenyl⟩—CH$_2$—<br>L=CH$_3$<br>R$^1$=—CH$_2$—<br>Z=COOC$_2$H$_5$ | 1730<br>1500<br>1240<br>1170<br>1030 | 1.10(6H,s), 1.25(3H,t), 2.73(2H,s), 3.23(2H,m), 3.53(2H,s), 4.23(2H,q), 4.43(1H,t), 6.86(2H,d), 7.2(7H,br) | 62.5–63.5° C (CH$_3$OH) | 1-(a) |

-continued $$Y-\underset{\underset{L}{|}}{\overset{\overset{L}{|}}{C}}-R^1-O-\underset{}{\bigcirc}-CH_2\underset{\underset{Cl}{|}}{C}H-Z$$

| No. | Product | IR spectrum (cm$^{-1}$, liquid film) | NMR spectrum (δppm, CDCl$_3$) | M.P. (°C) | Used Example |
|---|---|---|---|---|---|
| 5 | Y= ⟨phenyl⟩—<br>L=CH$_3$<br>R$^1$=—CH$_2$CH$_2$—<br>Z=—COOC$_2$H$_5$ | 1710<br>1515<br>1250<br>1030 | 1.17(3H,t), 1.35(6H,s),<br>2.11(2H,t), 3.15(2H,m), 3.75<br>(2H,t), 4.13(2H,q), 4.34<br>(1H,t), 6.6–7.5(9H,m) | Oil | 1-(a),<br>2 |
| 6 | Y= ⟨phenyl⟩—<br>L=CH$_3$—<br>R$^1$=—CH$_2$—<br>Z=—COOH | 1710<br>1510<br>1250<br>1040 | 1.30(6H,s), 2.8–3.4(2H,m),<br>3.87(2H,s), 4.39(1H,t),<br>6.7–7.5(9H,m), 10.2(1H,br) | Oil | 4 |
| 7 | Y= ⟨phenyl⟩—CO—<br>L=CH$_3$<br>R$^1$=—<br>Z=COONa | 1675<br>1610<br>1395<br>1235<br>1170<br>(KBr) | 1.60(6H,s), 2.77–3.60(2H,m),<br>4.23(1H,q), 6.67(2H,d),<br>7.03(2H,d), 7.37–8.37(5H,<br>m), (d$_6$-DMSO) | amorph. | 1-(b) |
| 8 | Y= ⟨phenyl⟩—CH$_2$—<br>L=CH$_3$—<br>R$^1$=—CH$_2$—<br>Z=—COONa | 1610<br>1520<br>1250<br>1040<br>(nujol) | 0.93(6H,s), 2.66(2H,s),<br>2,5–3.5(2H,m), 3.5(2H,s),<br>4.20(1H,q), 6.78(2H,d),<br>7.13(7H,br) (d$_6$-DMSO) | 168–169<br>(C$_2$H$_5$OH) | 1-(b) |
| 9 | Y= ⟨phenyl⟩—CH$_2$—<br>L=CH$_3$—<br>R$^1$=—CH$_2$—<br>Z=—COOH | 1720<br>1520<br>1250<br>1040<br>(nujol) | 1.00(6H,s), 2.70(2H,s),<br>NH 3,5(2H,s), 4.43<br>(1H,t), 6.83(2H,d), 7.13<br>(7H,br), 9.30(1H,s) | 91–92<br>(ligroin) | 1-(c)<br>4 |
| 10 | Y= ⟨phenyl⟩—CO—<br>L=CH$_3$<br>R$^1$=—CH$_2$—<br>Z=—COOC$_2$H$_5$ | 1740<br>1520<br>1250<br>1180 | 1.23(3H,t), 1.40(6H,s),<br>3.16(2H,m), 4.03(2H,s),<br>4.16(2H,q), 4.36(1H,t),<br>6.76(2H,d), 7.06(2H,d),<br>7.33(5H,br) | Oil | 1-(a) |
| 11 | Y=CH$_3$—<br>L=CH$_3$—<br>R$^1$=—CH$_2$—<br>Z=—COOC$_2$H$_5$ | 1740<br>1510<br>1245 | 0.98(9H,s),<br>1.20(3H,t),<br>3.18(2H,m),<br>3.53(2H,s),<br>4.17(2H,q),<br>4.38(1H,t),<br>6.83(2H,d),<br>7.13(2H,d) | 45–46 | 1-(a),<br>2 |
| 12 | Y=CH$_3$—<br>L=CH$_3$—<br>R$^1$=—CH$_2$—<br>Z=—COONa | 1620<br>1510<br>1250<br>(nujol) | 1.00(9H,s),<br>ca.3.1(2H,m),<br>3.57(2H,s),<br>4.23(1H,q),<br>6.79(2H,d),<br>7.19(2H,d),<br>(d$_6$-DMSO) | 191–192 | 1-(b) |
| 13 | Y=CH$_3$—<br>L=CH$_3$—<br>R$^1$=—CH$_2$—<br>Z=—COOH | 1720<br>1510<br>1250<br>(nujol) | 1.00(9H,s),<br>3.23(2H,m),<br>3.59(2H,s),<br>4.45(1H,t),<br>6.83(2H,d),<br>7.17(2H,d) | 96–97 | 1-(a),<br>1-(c) |
| 14 | Y=CH$_3$—<br>L=CH$_3$—<br>R$^1$=—CH$_2$—<br>Z=—CONH$_2$ | 3350<br>3150<br>1660<br>1500<br>1240<br>(nujol) | 1.00(9H,s),<br>3.26(2H,m),<br>3.60(2H,s),<br>4.50(1H,q),<br>6.20(2H,<br>broad),6.82<br>(2H,d),<br>7.20(2H,d) | 94–<br>95° C | 1-(a) |
| 15 | Y=CH$_3$CH$_2$CH$_2$—<br>L=CH$_3$—<br>R$^1$=—CH$_2$— | 1740<br>1510<br>1250 | 0.93(6H,s),<br>0.93(3H,t),<br>1.10(3H,t), | Oil | 1-(a) |

-continued

| No. | Product | IR spectrum (cm⁻¹, liquid film) | NMR spectrum (δppm, CDCl₃) | M.P. (° C) | Used Example |
|---|---|---|---|---|---|
|  | Z=—COOC₂H₅ |  | 1.3(4H,m), 3.13(2H,m), 3.51(2H,s), 4.05(2H,q), 4.30(1H,t), 6.73(2H,d), 7.05(2H,d) (CCl₄) |  |  |
| 16 | Y=CH₃— L=CH₃— R¹=—CH₂CH₂— Z=—COOC₂H₅ | 1740 1510 1240 | 1.00(9H,s), 1.21(3H,t), 1.70(2H,t), 3.20(2H,m), 4.06(2H,q), 4.23(2H,t), 4.40(1H,t), 6.80(2H,d), 7.10(2H,d) | Oil | 1-(a), 5 |
| 17 | Y=CH₃— L=CH₃— R¹=— Z=—COOC₂H₅ | 1740 1605 1505 1240 1160 | 1.17(3H,t), 1.30(9H,s), 2.86-3.53 (2H,m), 4.12(2H,q), 4.39(1H,t), 6.89(2H,d), 7.07(2H,d) | Oil | 1-(a) |
| 18 | Y=CH₃—⌬— L=CH₃— R¹=—CH₂— Z=—COOC₂H₅ | 1740, 1610, 1510, 1250 | 1.23(3H,t), 1.53(6H,s), 2.31(3H,s), 3.15(2H,m), 3.86(2H,s), 4.13(2H,q), 4.33(1H,t), 6.70(2H,d), 7.06(2H,d), 7.10-7.35 (4H,m) | Oil | 1-(a) |
| 19 | Y==CH₃—⌬— L=CH₃— R¹=—CH₂— Z=—COOH | 2500(sh) 1730 1620 1520 1250 1040 820 | 1.40(6H,s), 2.27(3H,s), 2.85-3.50(2H, m),3.88(2H,s), 4.42(1H,t), 6.75-7.43 (8H,m), 11.36(1H,s) | Oil | 1-(b) and 1-(c) |
| 20 | Y=CH₃O—⌬— L=CH₃— R¹=—CH₂— Z=—COOC₂H₅ | 1740 1515 1250 | 1.23(3H,t), 1.48(6H,s), 3.16(2H,m), 3.76(3H,s), 4.16(2H,s), 4.17(2H,q), 4.35(1H,t), 6.70-7.20 (8H,m) | Oil | 1-(a) |
| 21 | Y=Cl—⌬— L=CH₃— R¹=—CH₂— Z=—COOC₂H₅ | 1740 1520 1255 | 1.21(3H,t), 1.40(6H,s), 3.19(2H,s), 3.87(2H,s), 4.15(2H,q), 4.35(1H,t), 6.6-7.4(8H,m) | Oil | 1-(a) |
| 22 | Y=⌬—Cl L=CH₃— R¹=—CH₂— Z=—COOC₂H₅ | 1740 1520 1255 | 1.21(3H,t), 1.57(6H,s), 3.21(2H,m), 4.20(2H,q), 4.29(2H,s), 4.40(1H,t), 6.7-7.7 (8H,m) | Oil | 1-(a) |

EXAMPLE 8

(a) In 30 ml of isopropanol is dissolved 3.05 g of 2-chloro-3-[4-(2,2-dimethyl-2-phenylethyloxy)phenyl]-propionic acid, and 0.62 g of aluminum isopropoxide is added to the solution. The mixture is stirred at room temperature for 3 hours. Then, 0.5 ml of water is added to the mixture and the mixture is further stirred for 1 hour. The resulting precipitates are collected by filtration, washed with water and isopropanol and dried. The procedure gives 2.0 g of Aluminum 2-chloro-3-[4-(2,2-dimethyl-2-phenylethyloxy)-phenyl]propionate.

Elemental analysis: Calculated for $(C_{19}H_{20}O_3Cl)_3 Al_2(OH)_3$; C, 62.21; H, 5.77; Found: C, 62.03; H, 6.18.

IR spectrum (cm$^{-1}$, KBr); 3450(broad), 1610, 1520, 1250

(b) Isopropanol solution of aluminum isopropoxide is added to an aqueous isopropanol solution of 2-chloro-3-[4-(2,2-dimethyl-2-phenylethyloxy)phenyl]propionic acid to give aluminum 2-chloro-3-[4-(2,2-dimethyl-2-phenylethyloxy)-phenyl]propionate. Melting point: 220°-230° C Elemental analysis: Calculated for $(C_{19}H_{20}O_3Cl)_5Al_3(OH)_4$; C, 63.11; H, 5.80; Found: C, 63.25; H, 5.86.

IR spectrum (cm$^{-1}$, KBr): 3660, 3400(broad), 1620, 1520, 1250.

(c) Isopropanol solution of aluminum isopropoxide is added to anhydrous isopropanol solution of 2-chloro-3-[4-2,2-dimethyl-2-phenylethyloxy)phenyl]propionic acid to give aluminum 2-chloro-3-[4-(2,2-dimethyl-2-phenylethyloxy)-phenyl]propionate.

Melting point: 239°-240° C(decomp.)

Elemental analysis: Calculated for $(C_{19}H_{20}O_3Cl)_2 AlOH$; C, 64.49; H, 5.84; Found: C, 63.90; H, 6.25.

IR spectrum (cm$^{-1}$, KBr); 3450(broad), 1610, 1520, 1250

EXAMPLE 9

To 18.7 g of 2-chloro-3-[4-(2,2-dimethyl-2-phenylethyloxy)phenyl]propionic acid is added 6 ml of thionyl chloride, and the mixture is refluxed for 3 hours. The reaction mixture is concentrated under reduced pressure to distill off the unreacted thionyl chloride. To the resulting oily substance are added 7 g of urea, 40 ml of benzene and 5 drops of concentrated sulfuric acid, and the mixture is refluxed for 3 hours. After the solvent is distilled off, water is added to the residue. The resulting precipitates are collected by filtration, washed with water and dried. Recrystallization from ethanol gives 15 g of 1-[2-chloro-3-(4-<2,2-dimethyl-2-phenylethyloxy>phenyl)propionyl] urea as scales melting at 117°-118° C.

Elemental analysis: Calculated for $C_{20}H_{23}ClN_2O_3$; C, 64.08; H, 6.18; N, 7.47; Found: C, 64.32; H, 6.29; N, 7.37.

IR spectrum (cm$^{-1}$, nujol): 3370, 1620, 1180

NMR spectrum (δ ppm, CDCl$_3$): 1.47(6H,s), 3.27(2H,m), 3.93 (2H,s), 4.48(1H,t), 6.00(1H,broad), 6.83(2H,d), 7.17(2H,d), 7.40(5H,m), 8.10(1H,broad), 9.57(1H,s)

EXAMPLE 10

In a mixture of 1 ml of pyridine and 30 ml of tetrahydrofuran is dissolved 1.6 g of thiourea. To the mixture is added 10 ml of tetrahydrofuran solution of 3.8 g of 2-chloro-3-[4-(2,2-dimethyl-2-phenylethyloxy)phenyl]propionyl chloride under stirring and cooling with ice. The mixture is stirred under cooling with ice for 40 minutes, and the resulting precipitates are filtered off. The filtrate is concentrated and the concentrate is subjected to column chlomatography on silica gel (eluent: benzene/ethyl acetate=10/1). Recrystallization from 80% of ethanol solution gives 1.5 g of 1-[2-chloro-3-(4-<2,2-dimethyl-2-phenylethyloxy>phenyl)propionyl]-thiourea as scales melting at 111°-111.5° C.

Elemental analysis Calculated for $C_{20}H_{23}ClN_2O_2S$; C, 61.45; H, 5.93; N, 7.17; Found: C, 61.60; H, 6.03; N, 7.23.

IR spectrum (cm$^{-1}$, nujol); 3380, 3250, 3180, 1700, 1595, 1520, 1250

NMR spectrum (δ ppm, CDCl$_3$): 1.40(6H,s), 3.10-3.30(2H,m), 3.87(2H,s), 4.43(1H,q), 6.67-7.40(10H,m), 9.40(1H,broad), 9.67(1H,broad)

EXAMPLE 11

In 40 ml of benzene is dissolved 6.0 g of 1-[2-chloro-3-(4-<2,2-dimethyl-2-phenylethyloxy>phenyl)-propionyl]urea, and to the solution are added 0.3 g of zinc chloride and 2.0 g of acetic anhydride. The mixture is refluxed for 14 hours. After the solvent is distilled off, water is added to the residue. The resulting oily substance is extracted with ether and the ether layer is washed with water and dried. The resulting substance is subjected to column chromatography on silica gel. A mixture of benzene and ethyl acetate (9:1) was used as the eluent. Recrystallization from ethanol gives 1.6 g of N-acetyl-2-chloro-3-[4-(2,2-dimethyl-2-phenylethyloxy)-phenyl]propionamide melting at 125°-126° C.

Elemental analysis: Calculated for $C_{21}H_{24}ClNO_3$; C, 67,46; H, 6.47; N, 3.74; Found: C, 67.76; H, 6.52; N, 3.61.

IR spectrum (cm$^{-1}$, KBr): 3400, 3270, 3200, 1745, 1700, 1610

NMR spectrum (δ ppm, CDCl$_3$): 1.45(6H,s), 2.42(3H,s), 3.25 (2H,m), 3.94(2H,s), 4.63(1H,q), 6.86(2H,d), 7.16 (2H,d), 7.4(5H,m), 8.91(1H,s)

EXAMPLE 12

In 3 ml of toluene is dissolved 2.8 g of 2-chloro-3-[4-(2,2-dimethyl-2-phenylethyloxy)phenyl]propionamide, and to the solution are added 1.0 g of acetic anhydride and one drop of concentrated sulfuric acid. The mixed solution is stirred under heating at 100° to 110° C for 1.5 hour. After cooling, the solvent is distilled off and water is added to the residue. The resulting crystals are recrystallized from ethanol to give 2.8 g of N-acetyl-2-chloro-3-[4-(2,2-dimethyl-2-phenylethyloxy)phenyl]-propionamide.

EXAMPLE 13

By a similar manner to Example 9, the following compounds No. 1 to 10 are produced.

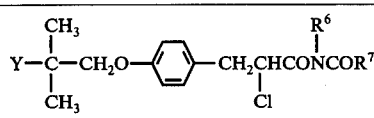

| No. | Product | IR spectrum (cm$^{-1}$, liquid film) | NMR spectrum (δppm,CDCl$_3$) | M.P. (° C) |
|---|---|---|---|---|
| 1 | Y=CH$_3$— R$^6$=H— R$^7$=—NH$_2$ | 3375, 3350, 3325, 1720, 1710, 1690, | 1.03(9H,s),3.10 (2H,m), 3.27(2H,s), 4.50(1H,t),6.10( | 158 – 159 |

-continued

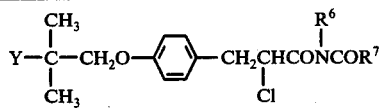

| No. | Product | IR spectrum (cm$^{-1}$, liquid film) | NMR spectrum (δppm, CDCl$_3$) | M.P. (° C) |
|---|---|---|---|---|
| | | 1610, 1590, 1250 (KBr) | 1H,br), 6.87(2H,d), 7.17(2H,d), 8.10 (1H,br), 9.63 (1H,s) | |
| 2 | Y= [phenyl]— <br> R$^6$=H— <br> R$^7$=CH$_3$— | 3400, 3270, 3200, 1745, 1700, 1610 (KBr) | 1.45(6H,s), 2.42 (3H,s), 3.25(2H,m), 3.94(2H,s), 4.63 (1H,q), 6.84(2H,d), 7.16(2H,d), 7.4(5H, m), 8.91(1H,s) | 125–126 |
| 3 | Y=CH$_3$—[phenyl]— <br> R$^6$=H <br> R$^7$=—NH$_2$ | 3400, 3325, 3250, 1710 (nujol) | 1.39(6H,s), 2.24 (3H,s), 3.30(2H, m), 3.83(2H,s), 4.30(1H,t), 5.90 (1H,br)7.97(1H, br), 6.7–7.4 (8H,m), 9.45 (1H,s) | 145–146 |
| 4 | Y=CH$_3$O—[phenyl]— <br> R$^6$=H— <br> R$^7$=—NH$_2$ | 3400, 3150, 1730, 1710 (nujol) | 1.35(6H,s), 3.20 (2H,m), 3.70(3H, s), 4.17(2H,s), 4.43(1H,t), 5.83(1H,br), 6.6–7.5(8H,m), 8.05(1H,br), 9.40(1H,s) | 136–137 |
| 5 | Y= [phenyl]— <br> R$^6$=H <br> R$^7$=—NHCH$_3$ | 3350, 3250 3120, 1700, 1690, 1560, 1520 (KBr) | 1.46(6H,s), 2.85 (3H,d), 3.20(2H, m), 3.88(2H,s), 4.45(1H,q), 6.75 (2H,d), 7.10(2H,d), 7.32(5H,m), 8.15 (1H,br), 9.99 (1H,s) | 125–126 |
| 6 | Y= [phenyl]— <br> R$^6$=H <br> R$^7$=—NH[phenyl] | 3240, 3130, 1710, 1565, 1515, 1450, 1250 (nujol) | 1.43(6H,s), 3.20–3.37(2H,m), 3.93 (2H,s), 4.53(1H, q), 6.73–7.60 (14H,m), 9.03 (1H,br), 10.40 (1H,br) | 101–103 |
| 7 | Y=Cl—[phenyl]— <br> R$^6$=H— <br> R$^7$=—NH$_2$ | 3350, 3230, 1695, 1520 (nujol) | 1.37(6H,s), 3.23 (2H,m), 3.87(2H, s), 4.47(1H,t), 5.93(1H,br), 6.7–7.5(8H,m), 8.05 (1H,br), 9.47 (1H,s) | 111–112 |
| 8 | Y= [phenyl]— <br> R$^6$=C$_2$H$_5$— <br> R$^7$=—NHC$_2$H$_5$ | 3320, 1710, 1520 | 1.03(3H,t), 1.13 (3H,t), 1.43(6H, s), 3.20(2H,m), 3.31(2H,q), 3.70 (2H,q), 3.90(2H,s), 4.67(1H,q), 6.7–7.5(9H,m), 8.87 (1H,t) | Oil |
| 9 | Y= [phenyl]—CH$_2$— <br> R$^6$=H <br> R$^7$=—N(CH$_3$)$_2$ | 3330, 1770, 1685, 1500 | 0.95(6H,s), 2.64 (2H,s), 2.97(6H, s), 3.24(2H,m), 3.47(2H,s), 4.64 (1H,q), 6.7–7.5 (9H,m), 8.93 (1H,s) | Oil |
| 10 | Y= [2-Cl-phenyl]— <br> R$^6$=H— <br> R$^7$=—NH$_2$ | 3335, 3230, 1695, 1520 (nujol) | 1.57(6H,s), 3.23 (2H,m), 4.27(2H, s), 4.43(1H,m), 5.80(1H,br), 6.7–7.5(8H,m), 8.03(1H,br), 9.37(1H,s) | 106–108 |

What is claimed is:

1. A compound of formula:

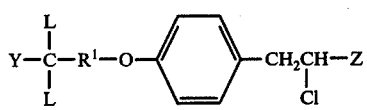

wherein Y stands for a lower alkyl group having 1 to 6 carbon atoms or a phenyl group, a benzoyl group or a phenylalkyl group having 7 to 11 carbon atoms, which may have a lower alkyl group having 1 to 3 carbon atoms, a lower alkoxy group having 1 to 3 carbon atoms or a halogen on the phenyl rings as a substituent; $R^1$ stands for a lower alkylene group having 1 to 4 carbon atoms or a valency bond; L stands for a lower alkyl group having 1 to 3 carbon atoms; and Z stands for COOR wherein R represents hydrogen or alkyl of from 1 to 4 carbon atoms.

2. A compound as claimed in claim 1, wherein Y is a lower alkyl group having 1 to 6 carbon atoms.

3. A compound as claimed in claim 1, wherein Y is a phenyl group, a benzoyl group or a phenylalkyl group having 7 to 11 carbon atoms, which may have a lower alkyl group having 1 to 3 carbon atoms, a lower alkoxy group having 1 to 3 carbon atoms or a halogen on the phenyl rings as a substituent.

4. A compound as claimed in claim 1, wherein L is methyl group.

5. A compound as claimed in claim 1, wherein the compound is 2-chloro-3-[4-(2,2-dimethyl-2-phenylethyloxy)phenyl]-propionic acid.

6. A compound as claimed in claim 1, wherein the compound is ethyl 2-chloro-3-[4-(2,2-dimethyl-2-phenylethyloxy)-phenyl]propionate.

7. A compound as claimed in claim 1, wherein the compound is sodium 2-chloro-3-[4-(2,2-dimethyl-2-phenylethyloxy)-phenyl]propionate.

8. A compound as claimed in claim 1, wherein the compound is 2-chloro-3-[4-(2,2-dimethylpropyloxy)-phenyl]propionic acid.

9. A compound as claimed in claim 1, wherein the compound is ethyl 2-chloro-3-[4-(2,2-dimethylpropyloxy)phenyl]-propionate.

10. A compound as claimed in claim 1, wherein the compound is sodium 2-chloro-3-[4-(2,2-dimethylpropyloxy)phenyl]-propionate.

11. A compound as claimed in claim 1, wherein the compound is 2-chloro-3-[4-(2,2-dimethyl-3-phenylpropyloxy)phenyl]-propionic acid.

12. A compound as claimed in claim 1, wherein the compound is ethyl 2-chloro-3-[4-(2,2-dimethyl-3-phenylpropyloxy)-phenyl]propionate.

13. A compound as claimed in claim 1, wherein the compound is sodium 2-chloro-3-[4-(2,2-dimethyl-3-phenylpropyloxy)-phenyl]propionate.

14. A compound as claimed in claim 1, wherein the compound is ethyl 2-chloro-3-[4-(1,1-dimethyl-2-phenylethyloxy)-phenyl]propionate.

15. A compound as claimed in claim 1, wherein the compound is ethyl 2-chloro-3-[4-(2,2-dimethylpentyloxy)phenyl]-propionate.